(12) United States Patent
Marx

(10) Patent No.: US 7,464,708 B2
(45) Date of Patent: Dec. 16, 2008

(54) DOSE INDICATORS AND DISPENSING CANISTER-INDICATOR ASSEMBLIES

(75) Inventor: Eduard Marx, Titz-Kalrath (DE)

(73) Assignee: 3M Innovative Properties Company, St. Paul, MN (US)

( * ) Notice: Subject to any disclaimer, the term of this patent is extended or adjusted under 35 U.S.C. 154(b) by 743 days.

(21) Appl. No.: 10/515,881

(22) PCT Filed: May 19, 2003

(86) PCT No.: PCT/US03/15924

§ 371 (c)(1),
(2), (4) Date: Nov. 24, 2004

(87) PCT Pub. No.: WO03/101514

PCT Pub. Date: Dec. 11, 2003

(65) Prior Publication Data

US 2005/0209558 A1    Sep. 22, 2005

(30) Foreign Application Priority Data

Jun. 3, 2002 (EP) .............................. 02012173.7

(51) Int. Cl.
*A61M 11/00* (2006.01)
(52) U.S. Cl. ............................ 128/205.23; 128/200.23; 128/203.12
(58) Field of Classification Search ............ 128/205.23, 128/200.23, 203.12, 203.15; 222/36, 38, 222/48
See application file for complete search history.

(56) References Cited

U.S. PATENT DOCUMENTS 3,187,748 A   6/1965  Mitchell et al.
3,456,644 A   7/1969  Thiel
3,456,645 A   7/1969  Brock
3,456,646 A   7/1969  Phillips et al.
3,565,070 A   2/1971  Hanson et al.

(Continued)

FOREIGN PATENT DOCUMENTS

DE            298 14 647 U1      1/2000

(Continued)

*Primary Examiner*—Steven O Douglas

(57) ABSTRACT

An annular dose indicator (50) for use with a dispenser comprising a dispensing canister (10) comprising a substantially cylindrical container (1) having a closed end (2) and an open end (3), said open end of the container being equipped with a dispensing means (4) that comprises an outlet member (5) movable between closed and discharge positions and an adaptor comprising a support block (21) having a socket (22) adapted to receive the outlet member, the container and support block being reciprocally movable relative to each other to cause the outlet member to move to its discharge position thereby dispensing a dose, said annular dose indicator (50) comprising an annular housing (60) having an interior surface (64) defining a substantially circumferential cavity; a counter-ring (80), said counter-ring located in the cavity and being arranged to be moveable relative to the housing by rotation about an axis parallel or substantially parallel to linear reciprocal movement of container and support block; a driving member (90) mounted on the interior surface of the housing, said driving member engaging the counter-ring and being arranged to be selectively engaged during reciprocal movement of container and support block as to drive an incremental, rotational movement of the counter-ring; wherein said indicator (50) is arranged to be circumferentially mountable about the dispensing-canister (10), such that the first edge (51) of the indicator faces towards the closed end of the container, the second edge (52) of the indicator faces towards the outlet of the dispensing canister, so that at least the outlet member of the canister will extend beyond the second edge of the indicator.

20 Claims, 9 Drawing Sheets

U.S. PATENT DOCUMENTS

| | | |
|---|---|---|
| 3,598,294 A | 8/1971 | Hedrick et al. |
| 3,605,738 A | 9/1971 | Ciranna |
| 3,636,949 A | 1/1972 | Kropp |
| 3,732,864 A | 5/1973 | Thompson et al. |
| 3,789,843 A | 2/1974 | Armstrong et al. |
| 3,814,297 A | 6/1974 | Warren |
| 5,174,473 A * | 12/1992 | Marelli ................ 222/38 |
| 5,349,945 A | 9/1994 | Wass et al. |
| 5,421,482 A | 6/1995 | Garby et al. |
| 5,482,030 A | 1/1996 | Klein |
| 5,611,444 A | 3/1997 | Garby et al. |
| 5,622,163 A | 4/1997 | Jewett et al. |
| 5,718,355 A | 2/1998 | Garby et al. |
| 5,799,651 A | 9/1998 | Garby et al. |
| 5,817,007 A | 10/1998 | Fodgaard et al. |
| 5,988,496 A | 11/1999 | Bruna |
| 6,082,358 A | 7/2000 | Scarrott et al. |
| 6,752,153 B1 | 6/2004 | Eckert |
| 7,191,918 B2 * | 3/2007 | Ouyang et al. ............ 222/36 |

FOREIGN PATENT DOCUMENTS

| | | |
|---|---|---|
| EP | 0 147 028 A1 | 7/1985 |
| EP | 0 254 391 A1 | 1/1988 |
| EP | 0 414 536 A2 | 2/1991 |
| EP | 0 480 488 | 4/1992 |
| EP | 0 480 488 A1 | 4/1992 |
| EP | 0 949 854 A1 | 10/1999 |
| GB | 1 269 554 | 4/1972 |
| GB | 1 290 484 | 9/1972 |
| GB | 1 317 315 | 5/1973 |
| GB | 1 335 378 | 10/1973 |
| GB | 1 392 192 | 4/1975 |
| GB | 2 061 116 A | 5/1981 |
| GB | 2 320 489 A | 6/1998 |
| WO | WO 92/09324 | 6/1992 |
| WO | WO 92/093232 | 6/1992 |
| WO | WO 92/17231 | 10/1992 |
| WO | WO 93/24167 | 12/1993 |
| WO | WO 95/34874 | 12/1995 |
| WO | WO 96/29278 | 9/1996 |
| WO | WO 98/41254 | 9/1998 |
| WO | WO 98/56444 | 12/1998 |
| WO | WO 99/57019 | 11/1999 |
| WO | WO 00/09187 | 2/2000 |
| WO | WO 00/59806 | 10/2000 |
| WO | WO 01/70313 A1 | 9/2001 |
| WO | WO 01/70314 A1 | 9/2001 |
| WO | WO 01/70315 A1 | 9/2001 |
| WO | WO 01/70316 A1 | 9/2001 |
| WO | WO 01/70317 A1 | 9/2001 |

* cited by examiner

DOSE INDICATORS AND DISPENSING CANISTER-INDICATOR ASSEMBLIES

CROSS REFERENCE TO RELATED APPLICATIONS

This application claims priority from European Application No. 02012173.7 filed Jun. 30, 2002, which was filed as PCT International Application No. PCT/US03/15924 on May 19, 2003.

1. Field of the Invention

The present invention relates to annular mechanical dose indicators, particularly suitable for use with medicinal dispensers, more particularly metered dose inhalers. The present invention also relates to dispensing canister-indicator assemblies, in particular such assemblies including medicinal aerosol dispensing canisters, more particular pressurized metered dose dispensing canisters, as well as dispensers comprising such dispensing canister-indicator assemblies.

2. Background of the Invention

Inhalation therapy is becoming an increasingly important method of administering medicaments to a patient. The medicament is generally formulated with suitable propellant and if appropriate other components and charged into a container, e.g. an aerosol vial. The container is typically fitted by means of a ferrule with a dispensing means, such a valve, in particular a metered dose valve, comprising an elongate outlet member (e.g. a valve stem) movable between closed and discharged positions, to provide a dispensing canister. The dispensing canister is typically used in conjunction with an adaptor, typically having a patient port, for example a mouthpiece or a port adapted for nasal use. The adaptor comprises a support block having a socket adapted to receive the outlet member of the dispensing means and an orifice having open communication with the socket and the patient port. The container and the support block are reciprocally movable relative to each other to allow the outlet member to move to its discharge position during the operation or firing of the device, thereby dispensing a dose.

With a conventional press-and-breathe device in which the patient fires the device by depressing the container towards the support block of the adaptor, while inhaling, a rough indication of the amount of medicament remaining in the vial can be obtained by shaking the whole unit. With experience, the user can distinguish the difference in 'feel' between a vial that is substantially full and one that is substantially empty. However, this method is necessarily far from precise and is even less satisfactory with a breath-actuated inhaler in which, because of the additional parts, the mass of the aerosol contents is a smaller proportion of the total unit weight. Thus, a difficulty arising from use of such known devices is that the patient cannot precisely determine the amount of medicament in the container at any given time. In extreme cases, a patient, possibly in an emergency situation and requiring an immediate dose of medicament, may find that the container will not dispense a dose because its contents have already been exhausted.

Although a number of dose counters or indicators for metered dose medicinal products have been proposed over the last decade, no pressurized metered dose inhaler with a built in dose counter has yet been marketed.

Proposed dose indicators include electrical and/or electronic dose counters, see for example U.S. Pat. No. 5,622,163 and WO 92/17231. Such counters can be disadvantageous in that they are relatively expensive. Furthermore, such counters require the use of a power source, such as a battery. Accordingly the reliability of such counters is overshadowed by the reliability of the power source itself. Here it is to be appreciated that some patients, e.g. asthma sufferers, often carry a device with them for extended periods of time and may only use the device on an occasional basis. If during this extended period the power source is exhausted or runs out, the patient would be again faced with uncertainty about the precise number of doses contained in the device.

A number of mechanical dose counters have also been proposed. Most of these counters comprise quite a number individual components and/or require significant modification of the inhaler device, in particular the adaptor. This makes mass production and assembly often complicated and/or tedious. A number of mechanical dose counters require additional counter-containing structures. For example, each of the documents, U.S. Pat. No. 5,421,482, U.S. Pat. No. 5,718,355, U.S. Pat. No. 5,817,007, U.S. Pat. No. 6,082,358, EP 0 254 391, EP 0 949 584, WO 95/34874 and WO 99/57019, relate to dose counting devices, which are provided on the exterior of an existing inhaler as an add-on counter-component. Such add-on counters suffer a number of disadvantages, including increased overall dimensions of the device resulting in a reduced ease in handling of the device.

GB 1,317,315, GB 1,290,484, GB 2,320,489, DE 298 14 647, U.S. Pat. No. 5,349,945, U.S. Pat. No. 5,482,030, WO 92/09324 and WO 98/56444, for example, relate to devices with dose counters located substantially beneath the container in a region near the outlet means of the dispensing means and near or around the support block of the adaptor. Such arrangements can be disadvantageous in that modification of the adaptor geometry, such as greater dimensions, in the critical region where atomization takes place is generally required. Furthermore, such counters are often not applicable for breath-actuated devices, because this region usually contains the trigger mechanism for the breath-actuated firing of the device.

WO 93/24167 for example proposes actuating means for triggering breath-actuated firing with an associated dose indicator as a type of add-on system at the end of the dispensing canister distant to the outlet member, which disadvantageously increases the overall dimensions of the device and correspondingly reduces general handleability of the device.

WO 00/59806 also relates to devices having an adaptor provided with a dose-indicating means.

EP 0 414 536 discloses a breath-actuated inhaler having an indicator with a ring mechanism located in the adaptor and mounted for rotation.

Another problem is that many dose counters do not differentiate between the same container being removed and put back in the adaptor (e.g. for cleaning) and a new container being inserted as a replacement, so that the count may or may not properly reset to the beginning.

SUMMARY OF THE INVENTION

Thus, there is an ongoing need for a simple, reliable, inexpensive, unobtrusive mechanical dose counter for use with a dispenser, such as a medicinal dispenser or more particularly a metered dose inhaler.

Moreover, there is a need for a mechanical dose counter for use with a dispenser comprising a dispensing canister comprising a substantially cylindrical container having a closed end and an open end, said open end of the container being equipped with a dispensing means that comprises an outlet member movable between closed and discharge positions and an adaptor comprising a support block having a socket adapted to receive the outlet member, the container and support block being reciprocally movable relative to each other to cause the outlet member to move to its discharge position thereby dispensing a dose.

According to one aspect of the invention there is provided an annular dose indicator comprising an annular housing having an interior surface defining a substantially circumferential cavity;

a counter-ring, said counter-ring located in the cavity and being arranged to be moveable relative to the housing by rotation about an axis parallel or substantially parallel to linear reciprocal movement of container and support block;

a driving member mounted on the interior surface of the housing, said driving member engaging the counter-ring and being arranged to be selectively engaged during reciprocal movement of container and support block as to drive an incremental, rotational movement of the counter-ring;

wherein said indicator is arranged to be circumferentially mountable about the dispensing-canister, such that the first edge of the indicator faces towards the closed end of the container, the second edge of the indicator faces towards the outlet of the dispensing canister, so that at least the outlet member of the canister will extend beyond the second edge of the indicator.

Typically, the two edges of the annular dose indicator are defined by the two edges of the annular housing.

Suitably the driving member is engaged by the adaptor, in particular an element thereof, during the reciprocal movement of the container and support block as to drive an incremental, rotational movement of the counter-ring. The incremental rotation of the counter-ring is suitably indicative of the successive dose firings.

The outer side of the counter-ring is preferably adjacent to the interior surface of the housing. The outer side of the counter-ring advantageously comprises indicia which are viewable through the housing to provide a visual indication of the total quantity of doses dispensed from, or remaining in, the container.

The indicator is preferably arranged such that the counter-ring is locatable about a portion of the container. Desirably the inner side of the counter-ring is adjacent to an exterior surface of the container.

More particularly, for use with dispensing canisters in which the container is equipped with a dispensing means by means of a ferrule, said ferrule having a seal-edge (an external edge of the ferrule near to where the open end of the container is sealed), the indicator is preferably arranged such that the counter-ring is locatable about a portion of the container and/or a portion of the ferrule. Desirably, the inner side of the counter-ring is adjacent to an exterior surface of the container and/or the ferrule. Preferably, the indicator is arranged, such that the second edge of the indicator is locatable near, more preferably adjacent to, the seal-edge of the ferrule.

The dose indicator desirably includes at least one stop member provided on the interior surface of the housing and engaging the counter-ring to prevent substantial movement of counter-ring along said axis. In another preferred embodiment the dose indicator further comprises at least one non-return member provided on the interior surface of the housing, said non-return member engaging the counter-ring to permit incremental rotation of the counter-ring in only one direction. The stop member and/or the non-return member are desirably integral with the housing, more desirably form-molded elements on the interior surface of the housing. Desirably, the stop member is integral with the non-return member, more desirably the stop member is simultaneously the non-return member.

Annular dose indicators according to the invention are advantageous in that the indicator can be manufactured independent of the dispensing-canister and the adaptor to provide a self-contained assembly. They can be easily mounted around the dispensing canister by sliding the indicator over the outlet- or container-end of the dispensing canister, as the case may be. This simplifies the production and handling of the indicator itself as well as the assembly of a complete dispenser or a dispensing-canister/indicator assembly. Production is also simplified in that the dose indicators according to the invention and in particular certain preferred embodiments thereof include a limited number of components. Because the counter-ring and driving member are located or mounted within the housing of the indicator, the sensitive components of the indicator are protected, providing desirable robustness, ease in handling as well as resistance to tampering during use.

In use, dose indicators according to the invention are located substantially about the dispensing-canister and above the outlet means, and thus the indicator can be advantageously used in both press-and-breathe inhalers and breath-actuated inhalers, in which the triggering or breath actuation mechanism is located near or about the support of the adaptor. Also because the indicators are positioned about the dispensing-canister, so that the first edge of indicator, which faces towards the closed end of the container, does not extend axially beyond the closed end of the container, a necessary increase in axial dimensions can be avoided, which is particularly advantageous in a portable inhaler.

Dose indicators according to the invention can be readily used with various types of dispensing canisters. Certain preferred embodiments of the dose indicator are particularly advantageous for use with dispensing canisters having a container, whose diameter of its outermost circumference is greater than the diameter of the outermost circumference of the ferrule and/or a container having a constricted portion, if applicable near or adjacent to the ferrule (distant to the outlet member). Here the space formed by the recess in the dispensing-canister-profile can be advantageously used for the components of the dose indicator, for example the counter-ring and thus the overall dimensions of the counter-ring and/or indicator can be kept in relation to the dispensing-canister to a minimum. Containing the dose indicator within the profile of the dispensing canister may also have an additional advantage of interfering less with the airflow through and within a dispenser or adaptor. In particular for use with such canisters, it is preferred that the diameter of the outermost circumference of the counter-ring is less than the diameter of the outermost circumference of the container.

It is preferred that the diameter of the outermost circumference of the indicator (typically the outermost circumference of the housing of the indicator) is less than, equal to or substantially equal to (i.e. ±up to 0.5 mm, more preferably ±up to 0.03 mm) the diameter of the outermost circumference of dispensing canister, in particular the container. More preferably the outermost circumference of the indicator, in particular the housing, is equal to or substantially equal to the outermost circumference of the dispensing canister.

Furthermore dose indicators, in particular the housing, can be advantageously secured to an external surface of the dispensing canister, preferably to an external surface of the container or, if applicable the ferrule of the dispensing canister, to provide a self-contained canister/indicator assembly.

The provision of a dispensing-canister/indicator assembly as a self-contained or single unit in which the indicator is located substantially about the dispensing canister (e.g. the container of the canister and/or the canister closure means)

and above the outlet means of the canister is particularly advantageous, because such an assembly is desirably robust. Furthermore such an assembly allows for desirable ease in handling and assembly of a complete dispenser. In particular, the insertion of the outlet means into the support block of an adaptor, is desirably facilitated for large scale assembly and more importantly, if desired, by a patient, because the outlet means of the dispensing-canister is unobstructed by components of a dose counter.

Accordingly, in another aspect of the present invention there is provided a canister-indicator assembly comprising a dispensing canister comprising a substantially cylindrical container having a closed end and an open end, said open end of the container being equipped with a dispensing means that comprises an outlet member movable between closed and discharge positions;

and an annular mechanical dose indicator mounted circumferentially about the dispensing-canister and secured to an external surface of the dispensing canister, such that the first edge of the indicator faces towards the closed end of the container and the second edge of the indicator faces towards the outlet of the dispensing canister, so that at least the outlet member of the canister extends beyond the second edge of the indicator.

Preferably the indicator is secured to an external surface of the container. In particular the indicator is desirably secured to the external surface of the container in the vicinity of the first edge of the indicator.

Preferred embodiments comprise a dispensing canister in which the container is equipped with a dispensing means by means of a ferrule, said ferrule typically having a seal-edge near the open end of the container. The indicator is preferably attached to an external surface of the ferrule or the container, more preferably the container. Preferably, the second edge of the indicator is located near, more preferably adjacent to the seal-edge of the ferrule. Desirably, the diameter of its outermost circumference of the container is greater than the diameter of the outermost circumference of the ferrule.

Preferably the diameter of the outermost circumference of the indicator is less than, equal to or substantially equal to (i.e. ±up to 0.5 mm, more preferably ±up to 0.3 mm) the diameter of the outermost circumference of the dispensing canister, in particular the container.

Canister-indicator assemblies according to the invention are particularly suitable for use with an adaptor comprising a support block having a socket adapted to receive the outlet member, the container and support block being reciprocally movable relative to each other to cause the outlet member to move to its discharge position thereby dispensing a dose from the container.

Desirably the annular mechanical dose indicator comprises an annular housing having an interior surface defining a substantially circumferential cavity;

a counter-ring, said counter-ring located in the cavity and being arranged to be moveable relative to the housing by rotation about an axis parallel or substantially parallel to linear reciprocal movement of container and support block; and a driving member mounted on the interior surface of the housing, said driving member engaging the counter-ring and being arranged to be selectively engaged during reciprocal movement of the container and support block as to drive an incremental, rotational movement of the counter-ring.

Another aspect of the present invention is a canister-indicator assembly in kit of parts form comprising a dispensing canister comprising a substantially cylindrical container having a closed end and an open end, said open end of the container being equipped with a dispensing means that comprises an outlet member movable between closed and discharge positions; and an annular mechanical dose indicator arranged to be mounted circumferentially about the dispensing-canister and secured to an external surface of the dispensing canister, such that the first edge of the indicator faces towards the closed end of the container and the second edge of the indicator faces towards the outlet of the dispensing canister, so that at least the outlet member of the canister extends beyond the second edge of the indicator.

A further aspect of the present invention is an annular mechanical dose indicator for use with a dispensing canister comprising a substantially cylindrical container having a closed end and an open end, said open end of the container being equipped with a dispensing means that comprises an outlet member movable between closed and discharge positions, said annular mechanical dose indicator being arranged to be mounted circumferentially about the dispensing-canister and secured to an external surface of the dispensing canister, such that the first edge of the indicator faces towards the closed end of the container and the second edge of the indicator faces towards the outlet of the dispensing canister, so that at least the outlet member of the canister extends beyond the second edge of the indicator.

In another aspect of the present invention, there is provided a dispenser for dispensing doses of medicament comprising a canister-indicator assembly as described above and an adaptor comprising a support block having a socket adapted to receive the outlet member of the dispensing-canister, the container and support block being reciprocally movable relative to each other to cause the outlet member to move to its discharge position thereby dispensing a dose from the container.

Desirably the adaptor, in particular an element thereof, is arranged to selectively engage the dose indicator, in particular an element thereof, during reciprocal movement of the container and support block as to drive an incremental count of the number of doses dispensed from or remaining in the container.

The adaptor preferably comprises an elongate or generally cylindrical portion extending opposite the support block defining a chamber, in which the dose indicator and at least a portion of the container of the canister-indicator assembly are locatable. Desirably the canister-indicator assembly is reversibly removable from the adaptor. In particular, the end of the cylindrical portion distant to the support block is unobstructed and the canister-indicator assembly can be reversibly inserted and removed from the chamber of the adaptor. There may be situations in which it is desired to minimize access to the dose indicator, dispensing-canister or possibly other internal components of a dispenser by the patient. In such cases, preferably the dose indicator and at least a portion of, more particularly the entire container are located within said chamber and the canister-indicator assembly is irremovable from the adaptor or sealed within the adaptor.

Preferably the adaptor comprises a patient port, wherein the support has an orifice having open communication with the socket and the patient port. The patient port may be detachable to allow washing and cleaning thereof. For those embodiments in which the adaptor includes an elongate or generally cylindrical portion, the detachable portion would preferably include the support block to facilitate washing and cleaning of the support block and the orifice. For such embodiments, desirably the dispensing canister-indicator assembly is non-removably located within the elongate or generally cylindrical portion of the adaptor.

The dispenser may be a non-pressurized metered dose pump spray dispenser or pressurized metered dose dispenser suitable for inhalation, nasal or sublingual administration of medicament. The dispenser is preferably a pressurized metered dose inhaler, more particularly a press-and-breathe inhaler or a breath-actuated inhaler.

These and other features, aspects, and advantages of the present invention will become better understood with regard to the following description, appended claims, and accompanying drawings.

DETAILED DESCRIPTION OF INVENTION

It is to be understood that the present invention covers all combinations of particular and preferred aspects of the invention described herein.

For a better understanding of the various aspects of the present invention, exemplary dispensing canisters suitable for use with the present invention as well as two exemplary conventional adaptors will be initially described in the following.

Figure 1A:
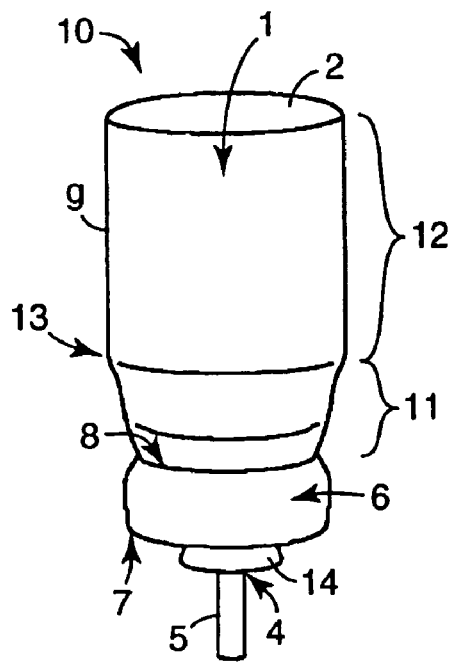
FIGS. 1a to c show isometric views of three exemplary dispensing canisters suitable for use in the invention.
Figure 1B:
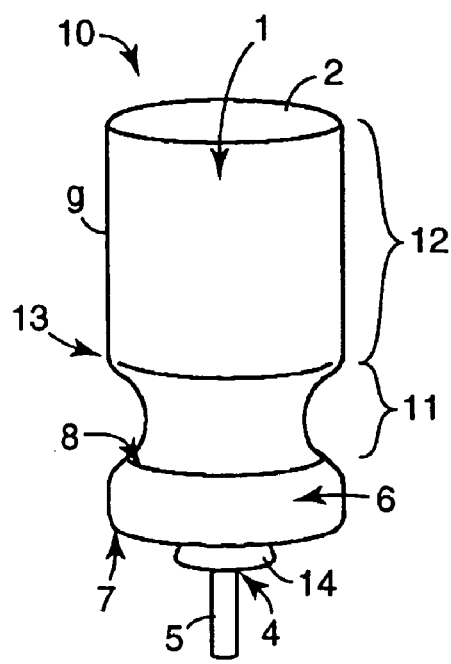
Figure 1C:
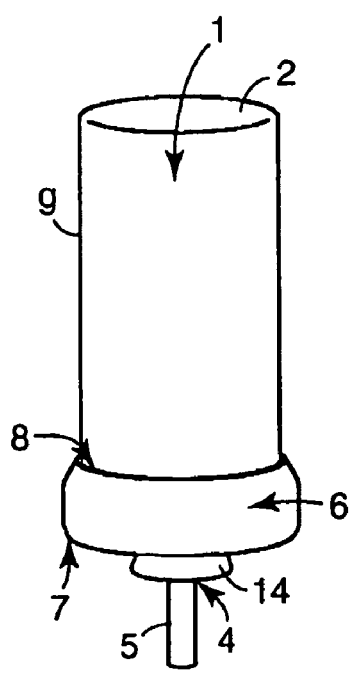

In FIGS. 1a to c three exemplary dispensing-canisters are illustrated. A dispensing canister (10) typically comprises a substantially cylindrical container (1), in particular an aerosol container, having a closed end (2), an open end (3, not visible) and a side-wall (9). The open end of the container is equipped with a dispensing means (4), in particular a dispensing valve, more particularly a metering dose valve, having an elongate outlet member (5), in particular a valve stem, movable between closed and discharged positions. The dispensing means is normally mounted onto the container by means of a ferrule (6). The ferrule is typically fastened onto the container by crimping, however it can be suitably fastened onto the container by other means, such as welding, adhesives, snap-fit, thread-fit. The term ferrule is understood here to mean any component or element of the dispensing canister, which is used to allow the attachment of the dispensing means to the container. The ferrule may be an integral component of the dispensing means or alternatively be a separate component, e.g. in the form of a mounting ring or cup. Alternatively the ferrule may be an integral component of the container, e.g. an element or extension of the container to allow the crimping or folding of the open end of the container over an appropriate element of the dispensing means. After fastening (e.g. crimping), the ferrule typically shows a seal-edge (7) (e.g. a folded edge) near the open end of the container and often a second edge (8) (e.g. a crimped edge) about the container (i.e. about the side wall (9) of the container). The portion of the dispensing-canister located between the seal-edge (7) of the ferrule and the elongate outlet member (5) is referred to as the nose (14) of the dispensing-canister. The height of the nose of the dispensing canister can vary from being relatively flat (ratio of axial height of nose to container <1:28), intermediate height (nose to container height ratio from 1:6 to 1:28) to being extended (nose to container height ratio >1:6). As can be seen in FIGS. 1a to c, the diameter of the outermost circumference of the ferrule may be less than, equal to or greater than the diameter of the outermost circumference of the container. The container (1) may have a constricted portion (11) distant to the closed end of the container (e.g. near or adjacent to ferrule) as depicted in FIGS. 1a and 1b, and a corresponding non-constricted portion (12) towards the closed end of the container; the boundary (13) between the constricted and non-constricted portions may be relevantly distinct or relevantly continuous. It is to be understood that FIGS. 1a to 1c show three exemplary dispensing canisters, which are suitable for use in the present invention, and that other dispensing canisters may also be suitable for use.

Figure 2A:
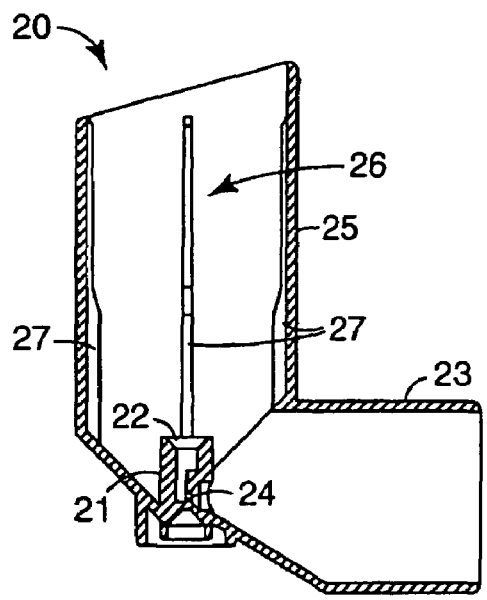
FIGS. 2a and 2b show vertical cross-sectional views of two exemplary, conventional adaptors; an adaptor for a press-and-breathe type inhaler and an adaptor for a breath-actuated inhaler.
Figure 2B:
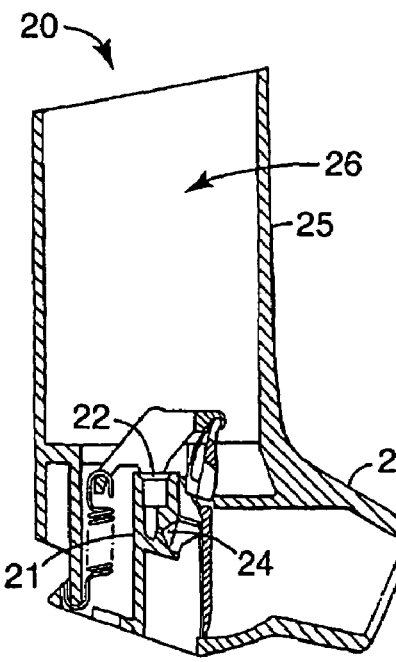
Figure 3:
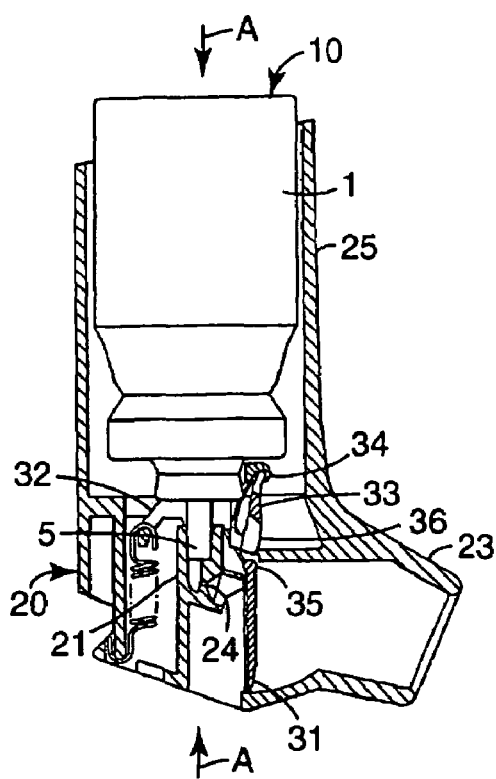
FIG. 3 shows a vertical cross-sectional view of a breath-actuated inhaler, i.e. the adaptor shown in FIG. 2b, containing a dispensing canister.

FIGS. 2a and 2b illustrate vertical cross-section views of two exemplary adaptors (20). FIG. 2a illustrates a conventional adaptor used for press-and-breathe type inhalers, while FIG. 2b depicts a conventional adaptor including a breath-actuation or triggering mechanism suitable for a breath-actuated inhaler. The adaptor comprises a support block (21) having a socket (22). The outlet member (5) of the dispensing-canister (10) (e.g. the dispensing end of the elongate valve stem of a metered dose dispensing valve) is received by the socket (22) and thus positioned in the support block (21), e.g. as illustrated in FIG. 3 showing the adaptor of FIG. 2b containing a dispensing-canister. The container (1) and the support block (21) are reciprocally movable relative to each other along an axis, marked as "A" in FIG. 3. The adaptor typically includes a patient port, such as a mouthpiece (23) and the support has an orifice (24) having open communication with the socket and the mouthpiece (23). The adaptor also typically includes an elongate or generally cylindrical portion (25) extending opposite the support block defining a chamber (26) to accommodate at least a portion of the container (1) of the dispensing-canister. One or more ribs (27) may be positioned within the chamber of the cylindrical portion to aid in locating and supporting the container in the correct position.

Referring to FIG. 3, the breath-actuation mechanism of the illustrated adaptor comprises a vane (31), which is pivotally mounted within the mouthpiece (23), a rocker element (32) which supports a catch (33) pivotally mounted on the rocker at (34). When a patient inhales through the mouthpiece, inhalation causes pivotal movement of the vane. The curved surface (35) of the vane (31) and the curved surface (36) of the catch (33) effectively acts as co-operating roller surfaces. Pivotal movement of the vane (31) causes the curved surface (35) to rotate in one direction resulting in curved surface (36) of the catch rotating in the opposite direction. This displacement of the catch moves from a blocking to an unblocking position allowing pivotal movement of the rocker element (32) which in turns allows movement of the container (1) relative to the support block (21) under the influence of the cocking pressure (e.g. the patient pressing downwards on the container) causing the valve to fire. The breath-actuation mechanism is described more in detail in EP 147 028, incorporated here by reference. Further examples of breath or inhalation activatable dispensers are described in British Patent Specification Nos. 1,269,554, 1,335,378, 1,392,192 and 2,061,116 and U.S. Pat. Nos. 3,456,644, 3,456,645, 3,456,646, 3,565,070, 3,598,294, 3,814,297, 3,605,738, 3,732,864, 3,636,949, 3,789,843 and 3,187,748 as well as WO 92/09323, WO 98/41254 and WO 01/70313 to 70317.

Figure 4:
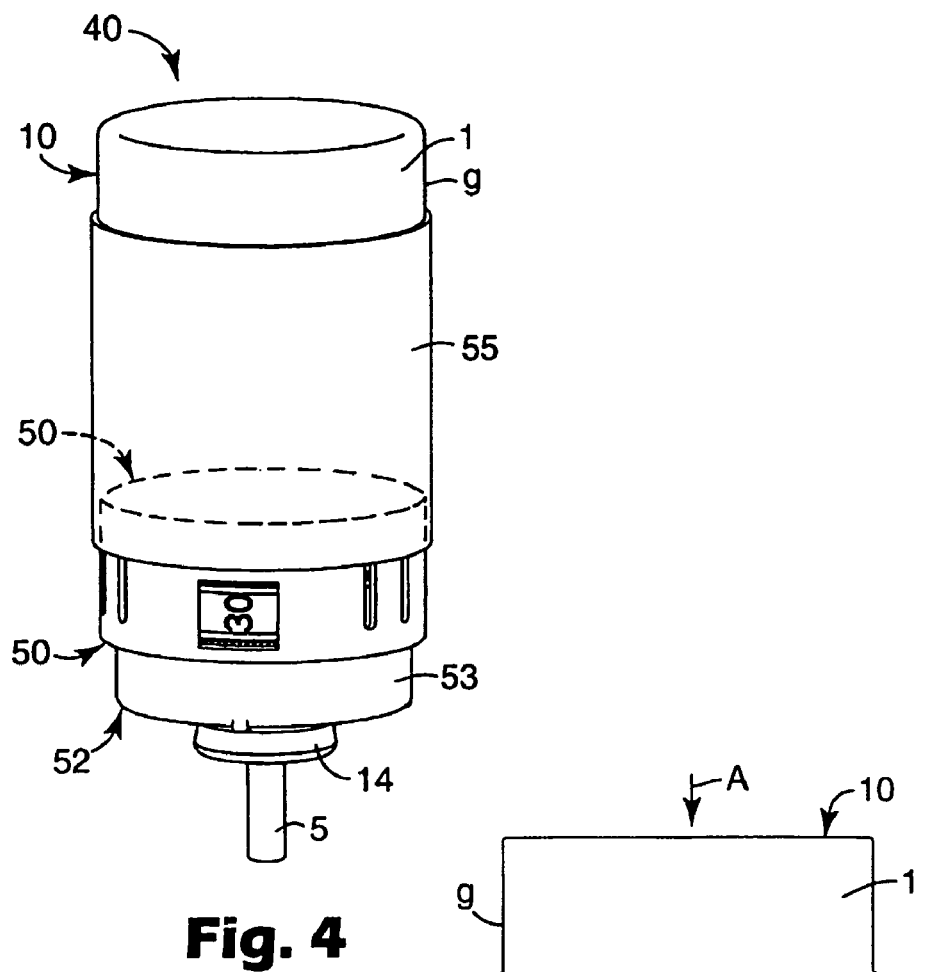
FIG. 4 shows an isometric view of a preferred embodiment of a canister-indicator assembly.

Referring to FIG. 4 showing an isometric view of a preferred embodiment of a canister-indicator assembly in accordance with the invention, the assembly (40) comprises a dispensing canister (10) and an annular mechanical dose indicator (50) having two edges (51,52). The indicator (50) is mounted circumferentially about the dispensing canister, such that the first edge (51) faces towards the closed end (2) of the container and the second edge (52) faces towards the outlet of the dispensing canister, so that at least the outlet member (5) of the canister extends beyond the second edge (52) of the indicator. Here, it is understood that the reference to the outlet member refers to the portion of the outlet member, which is located externally when the dispensing means is at rest (i.e. in its closed position). It is preferred that the entire portion of the outlet member extends beyond the second edge of the indicator.

Suitably, the container may be equipped with the dispensing means by means of a ferrule. The second edge (52) of the indicator is preferably located near, more preferably adjacent to, the seal-edge of the ferrule (not visible in FIG. 4).

As can be recognized in the preferred embodiment depicted in FIG. 4, the indicator (50) is secured directly to an external surface of the dispensing-canister (10), preferably an external surface of the container (1) (in particular an external surface of the side-wall (9) of the container), more preferably an external surface of the container in the vicinity of the first edge (51) of the indicator.

As shown in FIG. 4, the indicator may be secured by means an adhesive-coated film (55), which overlays an external surface (53) of the indicator, extending across the first edge (51) of the indicator, and the external surface of the side-wall of the container in the vicinity of said first edge. Alternatively, the indicator may be secured to an external surface of the ferrule. The indicator may be suitably secured by other means including shrink sleeves, heat forming, crimping and welding. Alternatively the indicator may be provided with a gripping member for securing the indicator onto an external surface of the container or the ferrule. To prevent tampering or detachment of the indicator, the indicator is preferably secured in a substantially non-reversible or substantially permanent manner. Preferred is the attachment of the indicator by adhesive or more preferably an adhesive-coated (in particular pressure-sensitive adhesive-coated) film. Suitable adhesives, in particular pressure-sensitive adhesives are typically chosen so as to provide a high adhesive or permanent bond to the particular substrate, e.g. indicator, container, ferrule, etc. For adhesive-coated films, a suitable film thickness ranges from 0.05 mm to 0.7 mm, more preferably 0.075 to 0.5 mm. The film may be made of any suitable material, such as paper, plastic. Desirably, the adhesive-coated film is provided in the form of a label or tape; more desirably a label or tape provided or printed with indicia concerning the product contained in the dispensing canister and/or indicia to aid the patient in reading an indication of the total quantity of doses dispensed from or remaining in the container.

The diameter of the outermost circumference of the indicator is preferably less than, equal to (e.g. as depicted in the preferred embodiment of FIG. 4) or substantially equal to the diameter of the outermost circumference of the dispensing canister. More preferably the diameter of outermost circumference of the indicator is equal to or substantially equal to the diameter of the outermost circumference of the container.

Figure 5:
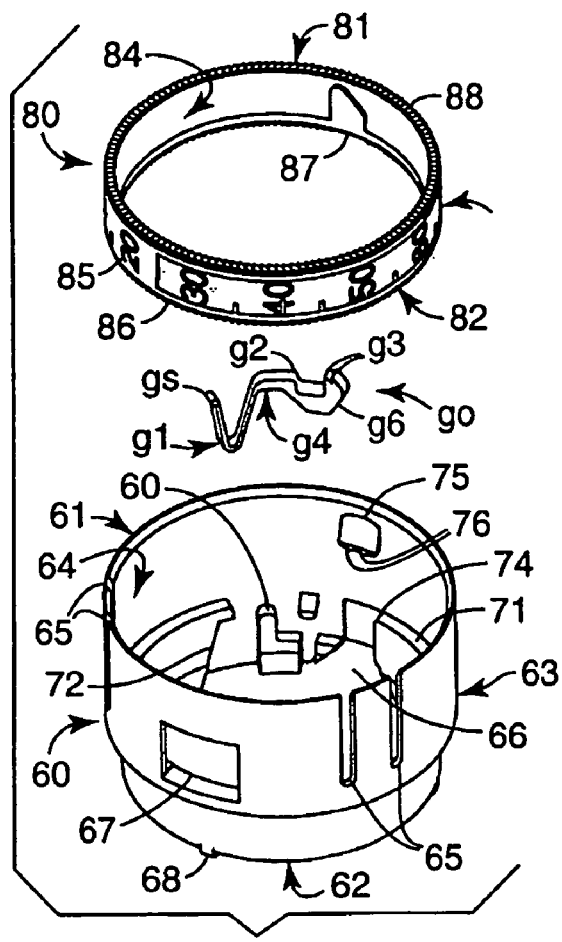
FIG. 5 shows an exploded view of a preferred embodiment of an annular dose indicator.
Figure 6:
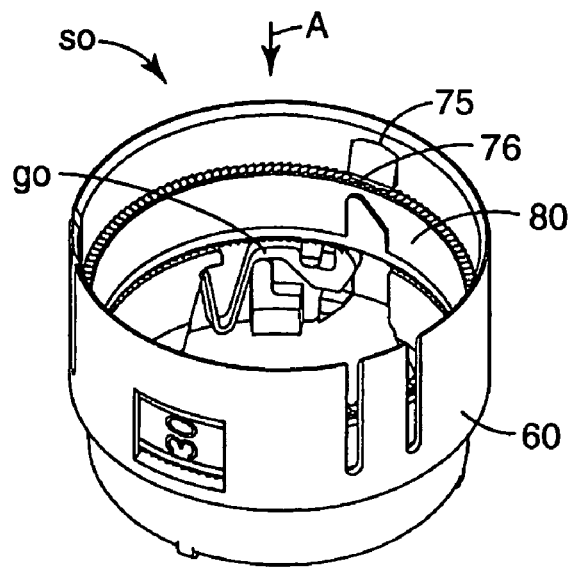
FIG. 6 shows an isometric view of the preferred annular dose indicator illustrated in FIG. 5.

The dispensing canister desirably comprises a container having constricted portion, in particular distant to the closed end of the container and a non-constricted portion towards the closed end of the container. The first edge of the indicator is desirably near or adjacent to the boundary between the constricted and non-constricted portion. In preferred embodiments comprising dispensing-canisters comprising a ferrule, desirably the diameter of the outermost circumference of the container is greater than the diameter of the outermost circumference of the ferrule FIGS. 5 and 6 show an exploded diagram and an isometric view, respectively, of a preferred embodiment of an annular dose indicator in accordance with the invention and an annular dose indicator suitable for use in canister-indicator assemblies according to the invention. As illustrated by the preferred embodiment shown in FIG. 5, the annular dose indicator (50) typically comprises three main components: an annular housing (60), a counter-ring (80) and a driving member (90).

The annular housing (60) has an interior surface (64) defining a substantially circumferential cavity. Although the housing is preferably in the form of a closed ring, as shown in FIG. 5, if desired the housing may alternatively have an open ring form (e.g. ¾ or ⅞ ring). The first and second edges (61, 62) of the annular housing are typically substantially parallel to one another and are generally continuous about the circumference of the housing. The housing may include one or more cut-out sections (65, 66) along the edges (61,62) for e.g. manufacturing and/or assembling purposes. The first and second edges (61, 62) of the housing typically define the first and second edges (51,52) of the indicator. The external surface (63) of the housing typically defines the external surface (53) of the indicator. The housing may include a folded lip or one or more radial protrusions (68) along the second edge (62).

The annular housing (60) may be made of any suitable rigid, durable material, such as metal, plastic or combinations of these materials. Plastic is preferred since it can be molded, preferably by high precision molding, into a finished piece and thereby may be less expensive to manufacture. Preferably the housing comprises a transparent or translucent plastic. Suitable plastics include rigid, ductile polymers having good impact strength, for example IZOD impact strength greater than or equal to 65 KJ/m$^2$, preferably greater than or equal to 70 KJ/m$^2$ as determined by the method ISO 180-4β. For optimal molding, the polymer desirably exhibits good melt flow behavior, for example a polymer having a melt temperature around 280° C. would desirably exhibit a melt volume-flow rate as determined by ISO 1133 at 300° C., 1.2 kg from 17 to 30 (preferably 17 to 22) cm$^3$/10 min. Polycarbonates are preferred. The housing is desirably provided with a window (67), optionally a magnifying window. The window may be formed as a cut-out portion of the housing, as a polished portion of the housing or as fitted window in the housing.

The internal surface (63) of the housing (60) may be provided with one or more additional, preferably integral, more preferably form-molded components. For example, the internal surface is desirably provided with a bearing element (70) to facilitate the mounting of the driving member (90) on the interior surface of the housing. The internal surface of the housing is desirably provided with an annular ridge (71) to help support and position the counter ring (80). The annular ridge is typically non-continuous having two longitudinal edges (72,73) extending towards the second edge (62) of the housing. A limit member (74) may also be desirably provided to facilitate movement of the driving member. The interior surface is preferably provided with at least one stop member (75). The preferred embodiment depicted in FIGS. 5 and 6 includes three stop members (75), one (visible) located towards the first edge (61) distant to the cut-out portion (66) and two (not visible) located between the two pairs of cut-out portions (65) along the first edge. As can be better seen in FIG. 6, the stop member engages the counter-ring in order to prevent substantial movement of the counter-ring along the axis about which the counter-ring is moveable by rotation. The interior surface is also desirably provided with at least one non-return member (76), typically in the form of one or more teeth, which engages the counter-ring to permit incremental rotation of the counter-ring in one direction. Preferably the non-return member (76) is integral with the stop member (75), more preferably the stop member (75) is simultaneously the non-return member (76). The stop member and/or the non-return member also desirably facilitate the biasing of the counter-ring into engagement with the driving member.

Thickness of housing, including components provided on the interior surface, typically ranges from 0.9 to 3 mm, preferably 1.1 to 2.5 mm, more preferably 1.2 to 1.7 mm, most preferably 1.4 to 1.6 mm. The wall thickness of the housing, i.e. excluding components provided on the interior surface, typically ranges from 0.3 to 1.0 mm, preferably 0.4 to 0.75 mm, more preferably about 0.4 to 0.6 mm, most preferably about 0.5 mm.

The counter-ring (80) has an inner (84) and outer (83) side. Although the counter-ring is preferably in the form of a closed ring, as shown in FIG. 5, if desired the counter-ring may alternatively have an open ring form (e.g. ¾ or ⅞ ring). As can be seen in FIG. 6, the counter-ring (80) is located in the cavity of the housing (60), preferably such that the outer side (83) of the counter-ring is adjacent to the interior surface (64) of the housing. The counter-ring (80) is arranged to be moveable relative to the housing (60) by rotation about an axis parallel or substantially parallel to the linear reciprocal movement of the container and support (e.g. axis depicted as "A" in FIG. 6). The outer side (83) of the counter-ring desirably comprises indicia (85), which are viewable through the housing, to provide a visual indication of the total quantity of doses dispensed from, or remaining in, the container of the dispensing-canister. The indicia may be suitably alphabetical, numerical, alphanumeric, or color symbols, providing a sequential count-up or count-down of dispensed doses or providing a more general indication, such as "Full", "Empty", etc.

The counter-ring has two edges (81, 82), the first edge (81) towards the first edge (61) of the housing and the second edge (82) towards the second edge (62) of the housing and the driving member (90). As can be see in FIGS. 5 and 6, the counter-ring desirably has a set of teeth (86) along the second edge (82) of the counter-ring and one or more teeth of the set of teeth (86) are in engagement with the driving member. The number of teeth in the set of teeth (86) is generally a function of the dispensing-canister in which the indicator is used with, in particular the number of doses to be dispensed from the dispensing-canister. Generally the set of teeth includes an appropriate number of teeth to allow for the counting of up to 220 doses, more preferably up to 190 doses, even more preferably up to 160 doses and most preferably up to 130 doses. Desirably the set of teeth (86) along the second edge includes a spacer gap and/or a spacer block (87) to prevent more than one full revolution of the counter-ring. In alternative embodiments in which the counter-ring is provided in the form of an open-ring, the gap in the open-ring would allow for the prevention of more than one full revolution. Desirably the counter-ring has a second set of teeth (88) along the first edge (81) of the counter-ring. One or more teeth of the second set of teeth (88) are preferably in engagement with the stop member (75) and/or non-return (76) member. As will be appreciated by those skilled in the art, the indicator may be arranged such that the non-return member may alternatively be in engagement with one or more teeth of the first set of teeth (86).

The counter-ring (60) may be made of any suitable rigid, durable material, such as metal, plastic or combinations of these materials. Again due to manufacture considerations and costs, plastic is preferred. Preferably the counter-ring comprises a printable polymer. The counter-ring is typically prepared by high precision molding. Preferably the polymer exhibits good melt flow behavior, for example a polymer having a melt temperature around 220 to 225° C. would desirably exhibit a melt volume-flow rate as determined by ISO 1133 at 250° C., 2.16 kg between 25 and 45 $cm^3$/10 min, preferably 37 to 42 $cm^3$/10 min. Polybutylene terephthalate (PBT) polymers are preferred.

The wall thickness of the counter-ring typically ranges from 0.4 to 2.0 mm, preferably 0.7 to 1.5 mm, more preferably 0.90 to 1.3 mm, most preferably about 0.95 mm.

As depicted in FIG. 6, the driving member (90) is mounted on the interior surface (64) of the housing. The driving member (90) engages the counter-ring (80), in particular the driving member desirably includes at least one pawl (93), preferably two or more pawls in engagement with teeth of the first set of teeth (86) of the counter-ring. As described in more detail below, the driving member is arranged to be selectively engaged, in particular by the adaptor, more particularly an element thereof, during reciprocal movement of the container and support block as to drive an incremental, rotational movement of the counter-ring. In particular, the driving member, as better seen in FIG. 5, preferably includes an V-shaped, spring portion (91), integral with a shallow U-shaped portion (92) including a pawl, preferably two pawls, (93) provided at the end of U-shaped portion distant to the spring portion.

It should be appreciated that the driving member of the preferred dose indicator of FIGS. 5 and 6 represents one possible form of a suitable driving member. Suitable driving members may be provided in a variety of suitable forms including one or more pawls for engagement with the counter-ring.

The driving member (90) may be made of any suitable durable material, such as metal, plastic or combinations of these materials, preferably plastic. For optimal molding, preferably high precision molding, the polymer desirably exhibits good melt flow characteristics. Suitable polymers includes polymers having a Young's modulus greater than or equal to 2500 MPa, preferably greater than or equal to 3000 MPa (as determined by ISO 527 parts I and II) and a tensile strain at break greater than or equal to 4%, preferably greater to or equal to 5.5% (as determined by ISO 527 parts I and II).

Preferred are PBT, poly-oxymethylene (POM) and LCP polymers. Desirably the material of each the driving member, housing and counter-ring is selected, such that the frictional behavior between the driving member and each the housing and counter-ring is low, preferably a substrate-substrate friction coefficient less than or equal to 0.3.

The thickness of the driving member, typically having substantially the same thickness as the counter-ring, generally ranges from 0.4 to 2.0 mm, preferably 0.7 to 1.5 mm, more preferably 0.90 to 1.3 mm, most preferably about 0.95 to 1.0 mm.

In assembly of the preferred indicator depicted in FIGS. 5 and 6, the driving member is mounted on the bearing element (70) at the interface (94) of the spring and pawl-bearing portions (91, 92) of the driving member. The end (95) of the spring portion (91) is positioned against a longitudinal edge (72) of the ridge (71), while the pawl-bearing portion (92), is positioned adjacent to and substantially about the limit member (74). The counter-ring (80) is then inserted into cavity of the housing (60), by sliding the counter-ring over the stop member or members (75). The cut-out portions (65) along the first edge (61) of the housing (60) facilitate the insertion of the counter-ring (80) by deflecting outwards. Once the counter-ring (80) is inserted beyond the stop member(s) (75) into engagement with the driving member (90), the stop member (s) prevent any substantially linear movement of the ring along axis "A".

Figure 7:
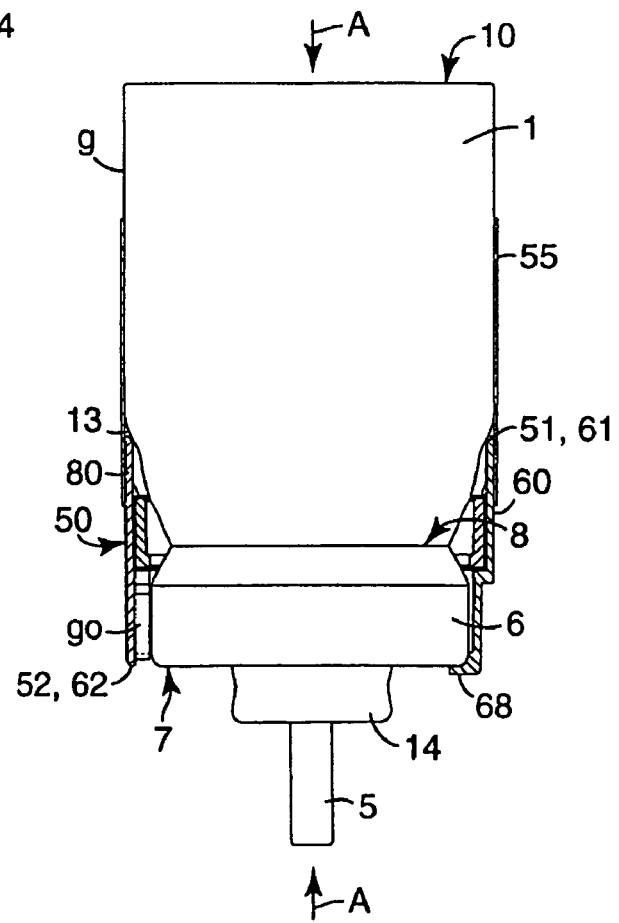
FIG. 7 shows a cross sectional view of the preferred annular dose indicator illustrated in FIGS. 5 and 6, mounted and attached to a dispensing canister of the type depicted in FIG. 1a, providing a preferred embodiment of a canister-indicator assembly.

FIG. 7 shows a partial, cross-sectional view of a preferred embodiment of a canister-indicator assembly. In particular, FIG. 7 shows the preferred dose indicator assembly as depicted in FIGS. 5 and 6 mounted and secured to a dispensing canister of the type depicted in FIG. 1a. As can be recognized from FIG. 7, the annular dose indicator (50) is mounted onto the dispensing canister (10) by sliding it over the dispensing canister, in particular over the outlet-end of the dispensing canister. The indicator, in particular the housing (60), is secured to the external surface of the dispensing canister (10), in particular the side wall (9) of the container (1) in the vicinity of the first edge of the indicator and housing (51,61) desirably by means of an adhesive-coated film (55) in a similar manner as described above. The indicator housing (60) is advantageously immovable in relation to the dispensing canister, enhancing overall robustness and handleability of the canister-indicator assembly. The first edge of the indicator and housing (51,61) is desirably located near the boundary (13) between the constricted and non-constricted portions of the container. The second edge of the indicator and housing (52, 62) is desirably located adjacent to the seal-edge (7) of the ferrule (6). To facilitate positioning of the indicator adjacent to the seal-edge of the ferrule, the second edge (62) of the housing (60) may be desirably provided with one or more radial protrusions (68). These protrusions advantageously facilitate positioning by providing a reference to aid the control of the relative positions of the indicator and an actuation pin so that manufactured assemblies operate within a narrow range of a specified counter actuation travel between the container and the support block. As can be seen in FIG. 7, the counter-ring (80) is desirably located about a portion (in particular a constricted portion) of the container (1) and a portion of the ferrule (6). The inner side of the counter-ring is desirably adjacent to an exterior surface of the container and ferrule. In alternative, preferred embodiments, the counter-ring may be located just about a portion of the container. The driving member (90) of the preferred embodiment depicted in FIG. 7 is located adjacent to an exterior surface of the ferrule (6).

In the embodiment illustrated in FIG. 7, both the nose (14) as well as the outlet means (5) extend beyond the second edge of the indicator. In alternative, preferred embodiments, the second edge of the indicator and housing may be located about the dispensing canister on a level (or height) near or adjacent to the level (or height) of the edge of the nose adjacent to the outlet means. The counter-ring may be desirably located about a portion of the ferrule or about a portion of the nose, the latter being particularly advantageous with dispensing canisters having extended noses.

As illustrated in FIG. 7, advantageously, the diameter of the outermost circumference of the indicator (50), in particular the housing (60), is equal to (or substantially equal to) the diameter of the outermost circumference of the container. For embodiments in which the counter-ring of the annular dose indicator is located about a portion of the container and/or the ferrule, the inner diameter of the counter-ring is typically greater than the diameter of the outermost circumference of the ferrule. For embodiments in which the counter-ring is located about the nose, the inner diameter of the counter-ring may be less the diameter of the ferrule. However for such embodiments it is preferred that inner diameter of the counter-ring is greater than the diameter of the outmost circumference of the ferrule. More particularly, for ease in manufacturing the counter-ring, it is preferred that the outer diameter of the counter-ring be large as possible, while still providing an indicator and housing having an outermost circumference whose diameter is equal to or substantially equal to the diameter of the outermost circumference of the container.

It is to be appreciated that the dimensions (e.g. outer and inner diameter, height, etc.) of the dose indicator and its respective components will be selected in consideration of the dimensions of particular dispensing canister, on which the indicator will be mounted. In order to provide one example of the possible dimensions of a dose indicator, in the following reference will be made to a dispensing canister and a dose indicator as illustrated in FIG. 7. For example, for a canister in which the diameter of the outermost circumference of the container (1) is 24.5 mm and the diameter of the outermost circumference of the ferrule (6) is 21 mm, a suitable diameter of the innermost circumference (excluding any radial protrusions (68)) of the indicator/housing (50,60) would be about 21.1 mm or greater, preferably about 21.1 to about 21.3 mm. A suitable diameter of the outermost circumference of the indicator/housing (50,60) would be about 24.0 to about 25 mm, preferably about 24.2 to 24.8 mm. For a canister in which the axial distance between the boundary (13) and the seal-edge (7) of the ferrule is 16.6 mm and the axial height of the constricted portion of the container is 10.6 mm, a suitable axial height of the housing would be about 12 to about 14.8 mm, preferably about 14 to 14.4 mm, while a suitable height of the counter-ring would be about 4.5 to about 4.9 mm.

It should be appreciated that although dose indicators according to the invention are particularly advantageous for use with dispensing-canisters in which the diameter of the outermost circumference of the ferrule is less than the diameter of the outermost circumference of the container, the indicators may be also be advantageous use with dispensing canisters in which the corresponding ferrule diameter is equal to or greater than the diameter of the outermost circumference of the container.

Figure 8A:
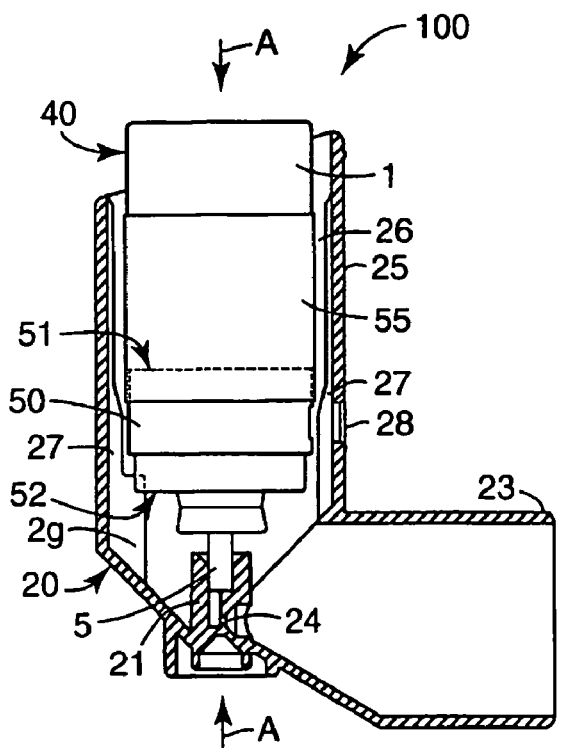
FIGS. 8a and b show vertical cross-sectional views of two preferred embodiments of a dispenser comprising a canister-indicator assembly illustrated in FIG. 7.

FIGS. 8a and b show vertical cross-sectional views of two preferred dispensers (100), in particular a press-and-breathe inhaler and a breath-actuated inhaler, respectively, in accordance with the invention; each dispenser comprises an adaptor and a canister-indicator assembly of FIG. 7.

Figure 8B:
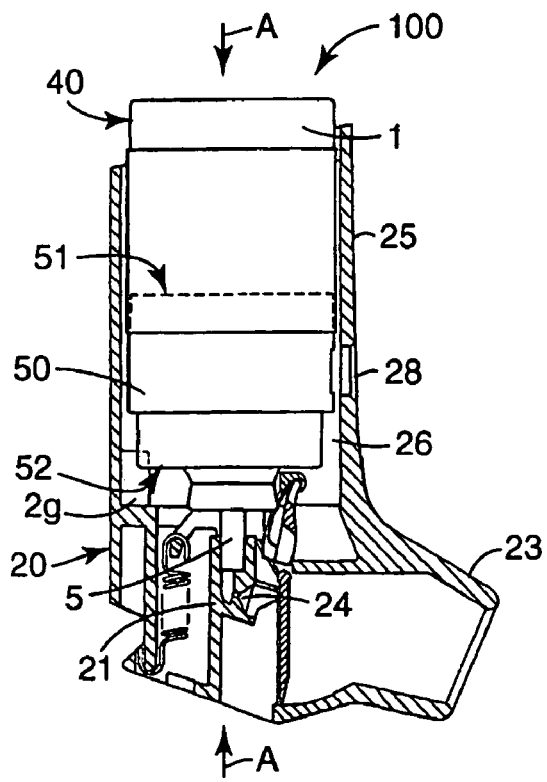

The adaptor (20) comprises a support block (21) having a socket (22) adapted to receive the outlet member (5) of the dispensing-canister (10). The container (1) and the support block (21) are reciprocally movable relative to each other along a linear axis, (marked as "A") to cause the outlet member to move to its discharge position thereby dispensing a dose from the container. The adaptor desirably includes a patient port, in particular a mouthpiece (23), and the support has an orifice (24) having open communication with the socket and the mouthpiece (23). The adaptor desirably includes an elongate or generally cylindrical portion (25) extending opposite the support block defining a chamber (26), in which the dose indicator (50) and at least a portion of the container (1) of the dispensing-canister are located or locatable. As can be appreciated from FIGS. 8a and b, the canister-indicator assembly is reversibly removable from the adaptor. In particular, the end of the elongate or generally cylindrical portion distant to the support block is unobstructed and the canister-indicator assembly can be reversibly inserted and removed from the chamber of the adaptor. As illustrated in FIG. 8b, the adaptor may desirably include a breath-actuation mechanism to provide a breath-actuated inhaler. (The components and the operation principle of the breath-actuation mechanism shown in FIG. 8b are discussed above in conjunction with the breath-actuated inhaler depicted in FIG. 3.)

In a comparison to the conventional press-and-breathe inhaler and breath-actuated inhaler adaptors illustrated in FIGS. 2a and 2b, it can be seen that the adaptors of the preferred dispensers shown in FIGS. 8a and 8b reveal a minimum of structural change. The adaptor (20), in particular the elongate or generally cylindrical portion (25) of the adaptor, is desirably provided with a window (28) to allow the user of the dispenser to read the indicia concerning the total quantity of doses dispensed from, or remaining in, the container of the dispensing-canister. For ergonomic reasons, the window of the adaptor (28) is desirably positioned at the front side of the adaptor, i.e. the side of the adaptor in which the patient port is located or locatable.

Desirably the adaptor, in particular an element thereof, is arranged to selectively engage the dose indicator, in particular the driving member, during reciprocal movement of the container and support block as to drive an incremental count of the number of doses dispensed from or remaining in the container. More particularly, the adaptor is advantageously provided with an actuation pin (29), typically as a form-molded element of the adaptor. In the embodiment shown in FIG. 8a, the actuation pin (29) is provided as an extension of a rib (27). While in the embodiments shown in FIGS. 8a and b, the actuation pin (29) is provided as a molded element of the adaptor, other embodiments can be envisaged in which the actuation pin (29) forms a part of the dose indicator itself.

When the outlet member (5) of the canister-indicator assembly (40) is inserted in the socket (22) of the support block (21), the actuation pin (29) is received within the dose indicator, e.g. passing through a cut-out portion (66) in the second edge (62) of the housing (see FIG. 5). During reciprocal linear movement (along axis "A") of the container and support block, the actuation pin (29), in particular the head of the actuation pin, selectively engages the driving member as to drive an incremental, rotational movement of the counter-ring. This is better understood by reference to FIGS. 9a to d, which show an enlarged view of the dose indicator in the region of the driving member as well as the actuation pin at various dispensing positions: at the rest or closed position; at a transitional position between the closed position and the final discharge position; at the final discharge position; and again at the closed position.

Figure 9A:
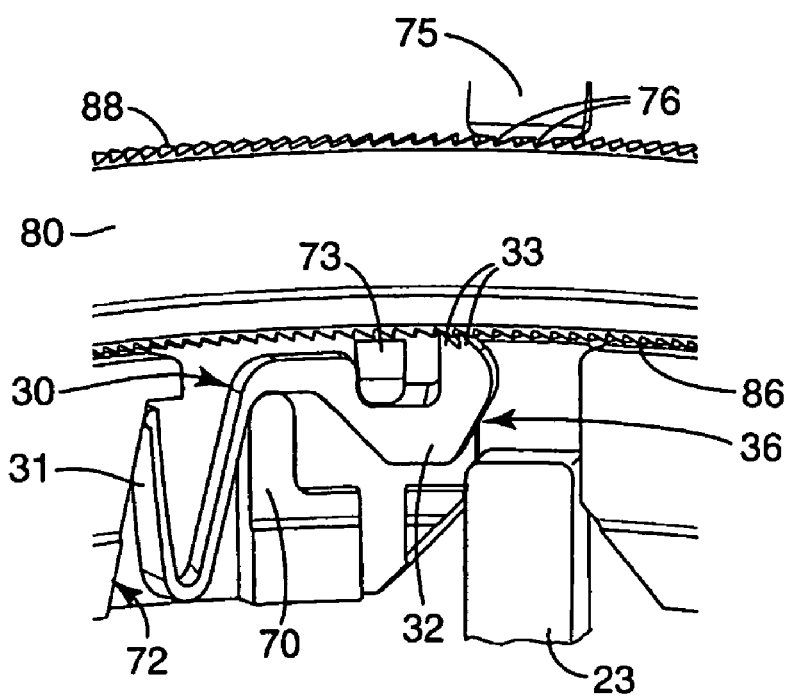
FIGS. 9a to d represent an enlarged, partial view of the preferred dispensers depicted in FIGS. 8a and 8b, showing the region of the driving member of the dose indicator at various dispensing positions.
Figure 9B:
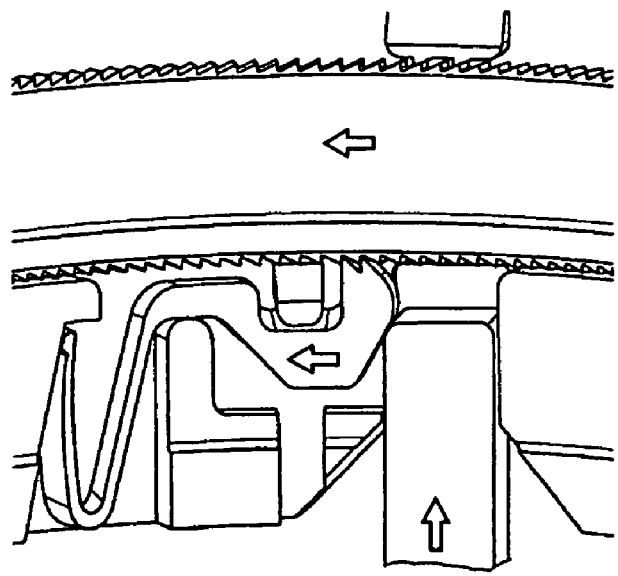
Figure 9C:
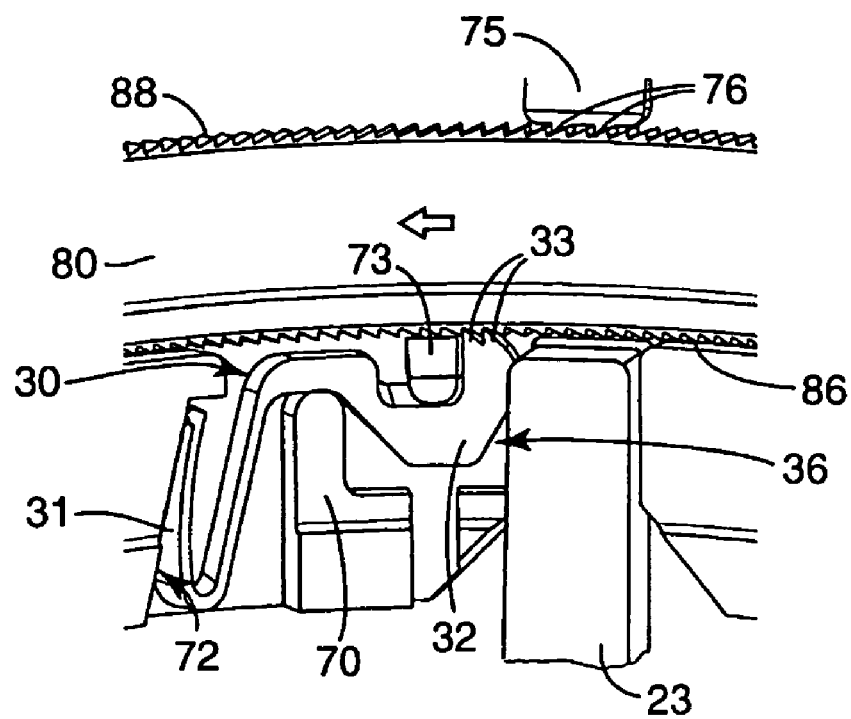

As illustrated in FIG. 9a, at the rest position, the head of the actuation pin (29) is located at a position adjacent an inclined receiving surface (96) of the pawl-bearing portion (92) of the driving member (90). The pawls (93) of the driving member are engaged with teeth of the first set of teeth (86) of the counter-ring (80), while the non-return member (76) in the form of two teeth (which is in this preferred embodiment simultaneously the stop member (75)) are engaged with teeth of the second set of teeth (88). As the container of the dispensing-canister moves towards the support block of the adaptor to allow the outlet member to move to its discharge position, the dose indicator moves towards the actuation pin (29), such that the head of the actuation pin moves, relative to the dose indicator, towards and engages the receiving surface (96) of the driving member (90) (see FIG. 9b). As the head of the actuation pin (29) moves along the receiving surface (96), the driving member (90), in particular the pawl-bearing portion (92) thereof, is urged to slide in a direction substantially perpendicular to the movement the actuation pin. This movement of the driving member in turn urges a rotational movement of the counter-ring (80). The limit member (73) desirably facilitates the sliding movement of the driving member in particular, to prevent over-movement of the driving member and correspondingly an over-rotation of the counter-ring. The prevention of an over-rotation of the counter-ring is also advantageously facilitated by the non-return member (76). As depicted in FIGS. 9b and 9c, during the rotation of the counter-ring, the teeth of the second set of teeth (88), with which the non-return member was originally engaged, moves past the non-return member, so that the non-return member moves into engagement with the next teeth at final discharge position. As can be seen, there is a squeezing action upon the counter-ring between the actuation pin and the non-return member, thus the angle of the inclined surface of each tooth of the non-return member is desirably smaller with respect to the horizontal than the angle of the receiving surface of the driving member.

Figure 9D:
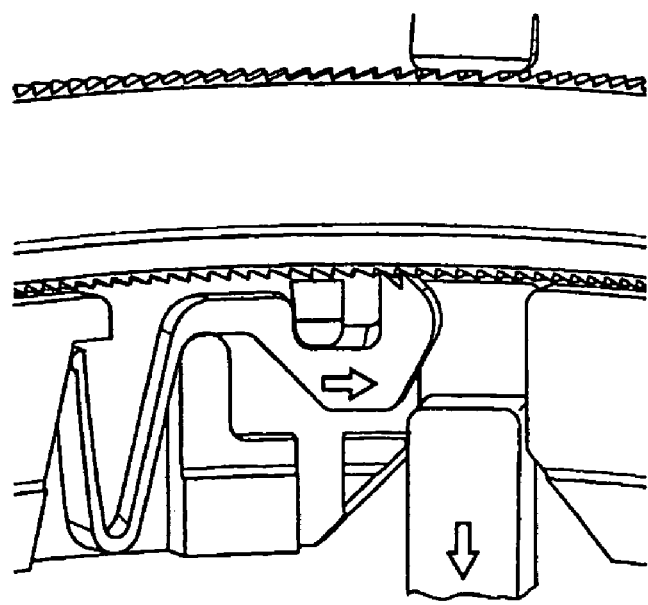

Upon return to the rest position (as the container of the dispensing-canister moves away from the support block), the dose indicator moves away from the actuation pin (29), such that the head of the actuation pin, in a relative movement, returns to its original position adjacent to the receiving surface (96) of the driving member (90) (see FIG. 9d). The tension on the spring portion (91) of the driving member (90) is released, allowing the driving member, in particular pawl-bearing portion (92) thereto, to slide in the opposite direction and thus moving the pawls (93) in engagement with next teeth of the first set of teeth (86) of the counter-ring (80). During this movement, the non-return member (76), which is in engagement with teeth of the second set of teeth (88) of the counter-ring (80), desirably aids in preventing rotational movement of the counter-ring.

Figure 10:
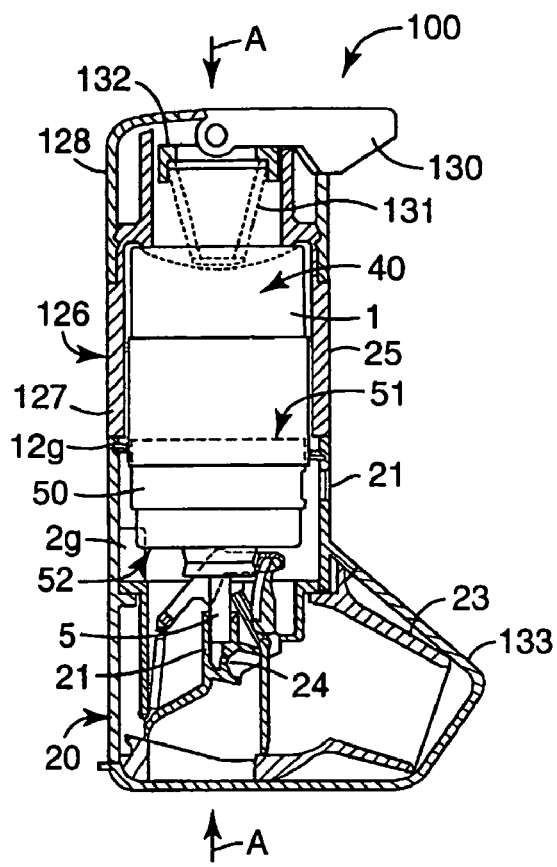
FIG. 10 shows a vertical cross-sectional view of a further preferred embodiment of a dispenser.

FIG. 10 shows a vertical cross-sectional view of a further preferred embodiment of a dispenser, in particular a breath-actuated inhaler provided with a cocking mechanism. This dispenser is similar to the dispenser shown in FIG. 8b. The dispenser (100) further comprises a housing (126) formed of a sleeve (127) and a crown (128), which can be mounted over the closed end of the container onto the adaptor (20), in particular the elongate or generally cylindrical portion (25) thereof, e.g. by a threaded coupling (129). To prevent tampering of the indicator (50) and/or the breath-actuation triggering mechanism, the housing can be desirably sealed or irreversibly coupled onto the adaptor, for example by welding, adhesives or by means of a one-way snap fit connection. In such embodiments, the dispensing canister-indicator assembly can not be removed from the adaptor. The cocking mechanism comprises a lever (130) which acts on a spring (131) facilitated by a spring guide (132). FIG. 10 shows the dispenser in the unprimed position. Upon pivoting the lever, downward pressure is applied to the aerosol container providing the cocking force for the breath-actuation firing of the dispenser. The dispenser may include a protective cover (133) for the mouthpiece (23).

Figure 11:
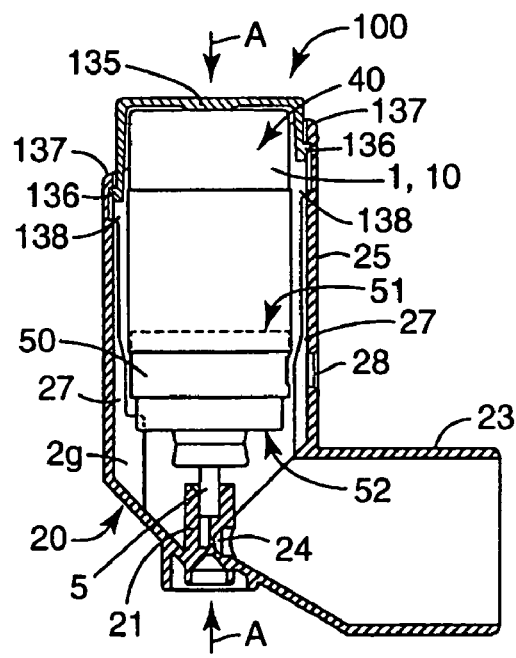
FIG. 11 shows a vertical cross-sectional view of another preferred embodiment of a dispenser.

FIG. 11 shows a vertical cross-sectional view of another preferred embodiment of a dispenser, in particular a press-and-breathe type inhaler. The dispenser is similar to the dispenser shown in FIG. 8a, but in this embodiment the dispenser (100) further comprises a cap (135), which is mounted, preferably irreversibly mounted, over the closed end of the container onto the adaptor (20), in particular the elongate or generally cylindrical portion (25) thereof, such that at least a portion of the cap is movable along axis "A" so that the dispenser-user can depress the dispensing canister (10), in particular the container (1), towards the support block (21) to dispense a dose. In the embodiment shown in FIG. 11, the connecting end of the cap preferably comprises an annular edge turned outward (136) connected to a corresponding annular edge (137) (typically turned inward) of the adaptor, in particular the elongate or generally cylindrical portion thereof, so as to prevent the separation of the cap from the adaptor. (The type of coupling is generally understood as a one-way snap fit coupling.) Thus, the canister-indicator assembly is non-removably located within the adaptor. The internal surface of the adaptor, in particular the elongate or generally cylindrical portion, is desirably provided with a guide portion or depression (138), to allow axial translation of the cap. Thus, in use as the container and cap are pressed downwards towards the support block, the annular edge (136) of the cap moves downwards within the guide portion (138). For airflow, slits (139, not shown) may be provided in the cap and/or in the adaptor in the vicinity of the support block.

Figure 12A:
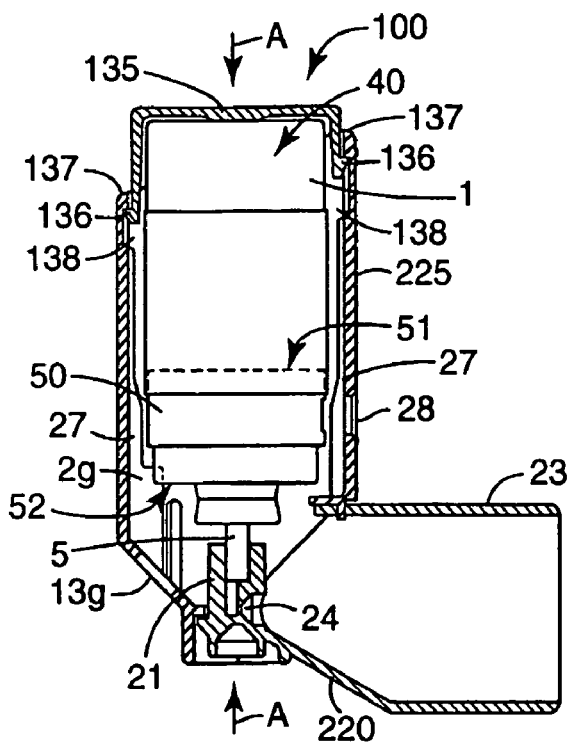
FIGS. 12 a and b shows a vertical cross-sectional view of an additional preferred embodiment of a dispenser.
Figure 12B:
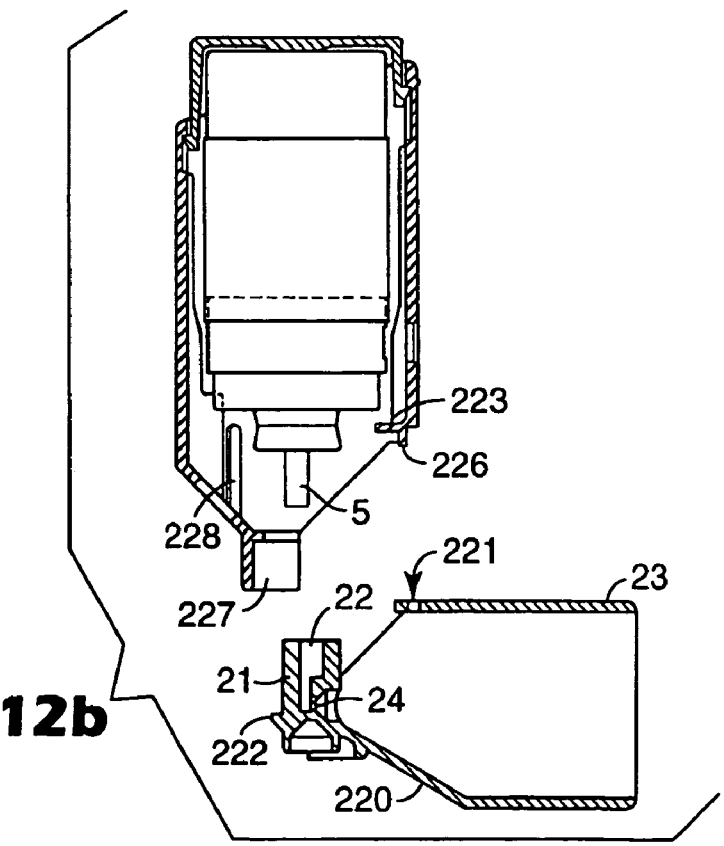

FIGS. 12a and b show vertical cross-sectional views of an additional preferred embodiment of a dispenser, in particular a press-and-breathe type inhaler. The dispenser shown in FIG. 12a comprises a canister-indicator assembly (40) of the type shown in FIG. 7 and an adaptor (20) comprising two parts: a support-portion (220) as well as an elongate or generally cylindrical portion or sleeve (225) defining a chamber or cavity adapted to receive the dispensing canister-indicator assembly (40). The support-portion (220), which comprises a patient port, in particular a mouthpiece (23) and a support block (21) having a socket (22) adapted to receive the outlet member of the dispensing-canister (10) and an orifice (24) having open communication with the socket and mouthpiece, is reversibly attachable and detachable. This can be best seen in FIG. 12b showing the dispenser with the support-portion detached. As can be recognized from FIGS. 12a and 12b, the support-portion (220) is attached to and detached from the dispenser by inserting and removing the outlet member (5) into and out of the socket block (21) of the support-portion. The support-portion is typically held securely in place due to the interference fit between the outlet member (5) and the socket (22) of the socket block. To facilitate positioning of the support-portion relative to the elongate or generally cylindrical portion, one or more positioning guides may be provided. For example, the support-portion (221) may include a guide slot (221) adapted to receive a guide pin (226) provided on the elongate or generally cylindrical portion (225) as the support-portion is attached or reattached. Alternatively or in conjunction thereto, the elongate or generally cylindrical portion may be provided with a guide groove (227) adapted to receive a guide notch (222) provided on the socket block, as the support portion is attached or reattached.

As shown in FIGS. 12a and b, one or more extensions (228) are desirably provided on the internal surface of the chamber to aid in retaining the canister-indicator assembly within the elongate or generally cylindrical portion as the support-portion is detached. During the detachment and reattachment of the support portion, the dispensing canister will typically be fired dispensing a dose, which will be counted by the indicator. As shown in FIGS. 12a and b, the dispenser preferably comprises a cap (135) irreversibly mounted over the closed end of the container onto the elongate or cylindrical portion (225), such that at least a portion of the cap is movable along axis "A" so that the dispenser-user can depress the dispensing canister (10), in particular the container (1), towards the support block (21) to dispense a dose. (The cap, elements thereof, etc. have been described above in connection with the dispenser embodiment shown in FIG. 11.) For airflow, slits (139) may be provided in the cap and/or in the adaptor in the vicinity of the support block. The dispensing canister-indicator assembly is thus advantageously non-removably located within the elongate or cylindrical portion of the adaptor, and thus desirably protected from e.g. tampering, while the support-portion of the adaptor, including the patient port and support block, is advantageously detachable from the dispenser for purposes of cleaning, etc.

Dispensers in accordance with the invention are suitable for dispensing medicament, in particular medicinal aerosol products e.g. suitable for administration to the lung by nasal or oral inhalation.

It will be understood that the present disclosure of particular preferred embodiments in accordance with the invention is for the purpose of illustration only and the invention extends to modifications, variations and improvements thereof.

The invention claimed is:

1. An annular dose indicator for use with a dispenser comprising (a) a dispensing canister comprising a substantially cylindrical container having a closed end and an open end, said open end of the container being equipped with a dispensing means that comprises an outlet member, having an outlet, movable between closed and discharge positions and (b) an adaptor comprising a support block having a socket adapted to receive the outlet member, the container and support block being reciprocally movable relative to each other to cause the outlet member to move to its discharge position thereby dispensing a dose from the container, comprising an annular housing having an interior surface defining a substantially circumferential cavity;

a counter-ring, said counter-ring located in the cavity and being arranged to be moveable relative to the housing by rotation about an axis substantially parallel to linear reciprocal movement of container and support block;

a driving member mounted on the interior surface of the housing, said driving member engaging the counter-ring and being arranged to be selectively engaged during reciprocal movement of container and support block as to drive an incremental, rotational movement of the counter-ring;

wherein said indicator is arranged to be slidably mountable about the dispensing canister and secured to an external surface of the dispensing canister, such that a first edge of the indicator faces towards the closed end of the container and a second edge of the indicator faces towards the outlet of the dispensing canister, so that at least the outlet member of the dispensing canister will extend beyond the second edge of the indicator.

2. An annular dose indicator according to claim 1, wherein the indicator is arranged such that the counter-ring is locatable about a portion of the container.

3. An annular dose indicator according to claim 1, wherein the outermost circumference of the indicator is less than, equal to or substantially equal to the diameter of the outermost circumference of the dispensing canister.

4. A dispensing canister-indicator assembly comprising a dispensing canister comprising a substantially cylindrical container having a closed end and an open end, said open end of the container being equipped with a dispenser that comprises an outlet member, having an outlet, movable between closed and discharge positions;

and an annular mechanical dose indicator mounted circumferentially about the dispensing canister and secured to an external surface of the dispensing canister, such that a first edge of the indicator faces towards the closed end of the container and a second edge of the indicator faces towards the outlet of the dispensing canister, so that at least the outlet member of the canister extends beyond the second edge of the indicator.

5. A canister-indicator assembly according to claim 4, wherein the indicator is secured to an external surface of the container.

6. A canister-indicator assembly according to claim 5, wherein the indicator is secured to the external surface of the container in the vicinity of the first edge of the indicator.

7. A canister-indicator assembly according to claim 4, in combination with an adaptor comprising a support block having a socket adapted to receive the outlet member, the container and support block being reciprocally movable relative to each other to cause the outlet member to move to its discharge position thereby dispensing a dose from the container, wherein the indicator comprises an annular housing having an interior surface defining a substantially cylindrical cavity;

a counter-ring, said counter-ring located in the cavity and being arranged to be moveable relative to the housing by rotation about an axis parallel or substantially parallel to linear reciprocal movement of container and support block; and a driving member mounted on the interior surface of the housing, said driving member engaging the counter-ring and being arranged to be selectively engaged during reciprocal movement of container and support block as to drive an incremental, rotational movement of the counter-ring.

8. A canister-indicator assembly according to claim 7, wherein the counter-ring is located about a portion of the container.

9. A canister-indicator assembly kit, comprising:

a dispensing canister comprising a substantially cylindrical container having a closed end and an open end, said open end of the container being equipped with a dispenser that comprises an outlet member, having an outlet, movable between closed and discharge positions; and an annular mechanical dose indicator arranged to be mounted circumferentially about the dispensing-canister and secured to an external surface of the dispensing canister, such that a first edge of the indicator faces towards the closed end of the container and a second edge of the indicator faces towards the outlet of the dispensing canister, so that at least the outlet member of the canister extends beyond the second edge of the indicator.

10. A canister-indicator assembly according to any one of claim 9, wherein the diameter of the outermost circumference of the indicator is less than or substantially equal to the diameter of the outermost circumference of the dispensing canister.

11. An annular mechanical dose indicator for use with a dispensing canister comprising a substantially cylindrical container having a closed end and an open end, said open end of the container being equipped with a dispensing means that comprises an outlet member, having an outlet, movable between closed and discharge positions, said annular mechanical dose indicator being arranged to be mounted circumferentially about the dispensing-canister and secured to an external surface of the dispensing canister, such that a first edge of the indicator faces towards the closed end of the container and a second edge of the indicator faces towards the outlet of the dispensing canister, so that at least the outlet member of the canister extends beyond the second edge of the indicator.

12. An annular mechanical dose indicator according to claim 11, wherein the diameter of the outermost circumference of indicator is less than or substantially equal to the diameter of the outermost circumference of the dispensing canister.

13. A dispenser for dispensing doses of medicament comprising a canister-indicator assembly according to claim 4, and an adaptor comprising a support block having a socket adapted to receive the outlet member of the dispensing-canister, the container and support block being reciprocally movable relative to each other to cause the outlet member to move to its discharge position thereby dispensing a dose from the container.

14. A dispenser according to claim 13, wherein the adaptor is arranged to selectively engage the dose indicator during reciprocal movement of the container and support block as to drive an incremental count of the number of doses dispensed from or remaining in the container.

15. A dispenser according to claim 13, wherein the adaptor further comprises an elongate or generally cylindrical portion extending opposite the support block defining a chamber, the dose indicator and at least a portion of the container of the canister-indicator assembly being locatable within said chamber.

16. A dispenser according to claim 15, wherein the canister-indicator assembly is reversibly removable from the adaptor.

17. A dispenser according to claim 15, wherein the dose indicator and at least a portion of the container of the canister-indicator assembly are located within said chamber and the canister-indicator assembly is irremovable from the adaptor.

18. A dispenser according to claim 13, wherein the adaptor further comprises a patient port and wherein the support has an orifice having open communication with the socket and the patient port.

19. A dispenser according to claim 18, wherein the patient port is detachable from the adaptor.

20. A dispenser according to claim 19, wherein a portion of the adaptor including the patient port and the support block is detachable from the adaptor.

* * * * *

UNITED STATES PATENT AND TRADEMARK OFFICE
CERTIFICATE OF CORRECTION

PATENT NO. : 7,464,708 B2
APPLICATION NO. : 10/515881
DATED : December 16, 2008
INVENTOR(S) : Eduard Marx Page 1 of 1

It is certified that error appears in the above-identified patent and that said Letters Patent is hereby corrected as shown below:

Column 4
Line 43, delete "aminimum" and insert -- a minimum --, therefor.

Column 10
Line 25, after "ferrule" insert -- . --.
Line 60, delete "180-4β" and insert -- 180-4A --, therefor.

Column 11
Line 25, delete "retum" and insert -- return --, therefor.
Line 28, delete "retum" and insert -- return --, therefor.

Signed and Sealed this

Eighteenth Day of August, 2009

David J. Kappos
*Director of the United States Patent and Trademark Office*